United States Patent
Stapleton

(10) Patent No.: US 10,687,676 B2
(45) Date of Patent: Jun. 23, 2020

(54) MICROGRAVITY URINE COLLECTION AND STORAGE

(71) Applicant: HAMILTON SUNDSTRAND CORPORATION, Charlotte, NC (US)

(72) Inventor: Thomas J. Stapleton, Southwick, MA (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 461 days.

(21) Appl. No.: 15/618,605

(22) Filed: Jun. 9, 2017

(65) Prior Publication Data
US 2018/0353020 A1    Dec. 13, 2018

(51) Int. Cl.
| | |
|---|---|
| A61F 5/455 | (2006.01) |
| A61F 5/44 | (2006.01) |
| A47K 11/12 | (2006.01) |
| A61F 5/441 | (2006.01) |
| A61L 9/14 | (2006.01) |
| B01D 46/36 | (2006.01) |
| B01D 46/54 | (2006.01) |
| B01D 46/00 | (2006.01) |
| B01J 20/20 | (2006.01) |
| A61L 9/014 | (2006.01) |
| F16K 31/44 | (2006.01) |

(Continued)

(52) U.S. Cl.
CPC ............... *A47K 11/12* (2013.01); *A61F 5/44* (2013.01); *A61F 5/4401* (2013.01); *A61F 5/441* (2013.01); *A61F 5/4405* (2013.01); *A61F 5/455* (2013.01); *A61F 5/4556* (2013.01); *A61L 9/014* (2013.01); *B01D 46/0036* (2013.01); *B01D 46/543* (2013.01); *B01J 20/20* (2013.01); *F16K 3/02* (2013.01); *F16K 15/00* (2013.01); *F16K 31/44* (2013.01)

(58) Field of Classification Search
CPC combination set(s) only.
See application file for complete search history.

(56) References Cited

U.S. PATENT DOCUMENTS 1,898,104 A * 2/1933 Thompson .............. A61F 5/453
   604/348
2,397,257 A * 3/1946 Goland ................ A61M 1/0011
   604/131

(Continued)

FOREIGN PATENT DOCUMENTS

EP    0327468    8/1989

OTHER PUBLICATIONS

European Patent Office, European Search Report dated Oct. 9, 2018 in Application No. 18177014.0-1122.

*Primary Examiner* — Tatyana Zalukaeva
*Assistant Examiner* — Guy K Townsend
(74) *Attorney, Agent, or Firm* — Snell & Wilmer L.L.P.

(57) ABSTRACT

A microgravity urine collection apparatus may include a bellows defining an internal chamber having a selectively adjustable volume. The bellows may include an inlet and an outlet. The microgravity urine collection apparatus may further include a first valve coupled to the bellows and configured to selectively control fluid flow through the inlet. The microgravity urine collection apparatus may also include a second valve coupled to the bellows and configured to allow fluid flow out of the bellows via the outlet and prevent fluid flow into the bellows via the outlet.

17 Claims, 7 Drawing Sheets

(51) Int. Cl.
*F16K 15/00* (2006.01)
*F16K 3/02* (2006.01)

(56) References Cited

U.S. PATENT DOCUMENTS

| | | | | |
|---|---|---|---|---|
| 3,421,504 A * | 1/1969 | Gibbons | A61M 1/0011 | 604/73 |
| 3,742,952 A * | 7/1973 | Magers | A61M 1/0011 | 604/133 |
| 3,774,611 A * | 11/1973 | Tussey | A61M 1/0011 | 604/133 |
| 4,202,058 A * | 5/1980 | Anderson | A61F 5/455 | 4/144.3 |
| 4,468,226 A * | 8/1984 | Kurtz | A61M 1/0013 | 137/205 |
| 4,529,402 A * | 7/1985 | Weilbacher | A61M 1/0011 | 137/625.41 |
| 4,642,088 A * | 2/1987 | Gunter | A61M 1/02 | 604/6.15 |
| 4,781,707 A * | 11/1988 | Boehringer | A61M 1/0013 | 604/317 |
| 4,950,247 A * | 8/1990 | Rosenblatt | A61M 1/0011 | 128/202.29 |
| 5,010,599 A * | 4/1991 | Nilsson | A61G 9/006 | 4/144.2 |
| 5,019,059 A * | 5/1991 | Goldberg | A61M 1/0011 | 604/317 |
| 5,102,404 A * | 4/1992 | Goldberg | A61M 1/0011 | 604/317 |
| 5,342,329 A * | 8/1994 | Croquevielle | A61M 1/0009 | 600/579 |
| 5,370,637 A * | 12/1994 | Brodeur | A61F 5/4556 | 4/144.3 |
| 5,438,721 A * | 8/1995 | Pahno | A61G 7/0005 | 4/480 |
| 5,495,870 A * | 3/1996 | Dorta | A47G 19/2227 | 137/588 |
| 5,549,584 A * | 8/1996 | Gross | A61M 1/0088 | 604/313 |
| 5,713,880 A * | 2/1998 | Anderson | A61F 5/453 | 604/349 |
| 5,902,253 A * | 5/1999 | Pfeiffer | A61B 5/145 | 600/573 |
| 6,183,454 B1 * | 2/2001 | Levine | A61F 5/4556 | 4/144.3 |
| 6,342,049 B1 * | 1/2002 | Nichols | A61F 5/4553 | 604/327 |
| 7,186,245 B1 * | 3/2007 | Cheng | A61F 5/44 | 604/349 |
| 7,823,807 B1 * | 11/2010 | Bauer | A01C 23/003 | 239/159 |
| 8,287,507 B2 * | 10/2012 | Heaton | A61M 1/0011 | 604/313 |
| 8,641,692 B2 * | 2/2014 | Tout | A61M 1/0003 | 604/316 |
| 9,187,190 B1 * | 11/2015 | Stapleton | B01D 46/00 | |
| 9,272,095 B2 * | 3/2016 | Felts | A61M 5/3129 | |
| 9,586,843 B2 * | 3/2017 | Morrison | C02F 1/688 | |
| 10,384,203 B2 * | 8/2019 | Yantz | A61B 5/150274 | |
| 2001/0031947 A1 * | 10/2001 | Heruth | A61M 5/14276 | 604/142 |
| 2002/0000253 A1 * | 1/2002 | Fillmore | A61M 27/00 | 137/607 |
| 2004/0002270 A1 * | 1/2004 | Courtney | B63C 9/0005 | 441/40 |
| 2005/0175665 A1 * | 8/2005 | Hunter | A61K 45/06 | 424/423 |
| 2005/0277912 A1 * | 12/2005 | John | G16H 20/17 | 604/890.1 |
| 2007/0208134 A1 * | 9/2007 | Hunter | A61F 2/0077 | 525/54.1 |
| 2007/0299043 A1 * | 12/2007 | Hunter | A61F 2/0077 | 514/171 |
| 2008/0108977 A1 * | 5/2008 | Heaton | A61M 1/0011 | 604/543 |
| 2008/0199851 A1 * | 8/2008 | Egan | B01L 3/5023 | 435/5 |
| 2008/0227073 A1 * | 9/2008 | Bardsley | G09B 23/30 | 434/267 |
| 2010/0028442 A1 * | 2/2010 | Archambeau | A61K 31/573 | 424/489 |
| 2010/0297193 A1 * | 11/2010 | Archambeau | A61K 9/0048 | 424/400 |
| 2010/0318116 A1 * | 12/2010 | Forsell | B01D 46/0065 | 606/200 |
| 2010/0323343 A1 * | 12/2010 | Egan | C12Q 1/6804 | 435/5 |
| 2011/0066254 A1 * | 3/2011 | Forsell | A61M 1/1068 | 623/23.64 |
| 2011/0087337 A1 * | 4/2011 | Forsell | A61B 17/12 | 623/23.68 |
| 2012/0046203 A1 * | 2/2012 | Walsh | A61K 5/150503 | 506/39 |
| 2013/0158482 A1 * | 6/2013 | Davis | A61B 5/150022 | 604/173 |
| 2014/0163664 A1 * | 6/2014 | Goldsmith | A61B 17/00491 | 623/1.11 |
| 2014/0325746 A1 * | 11/2014 | Block | A61F 5/455 | 4/144.3 |
| 2015/0223923 A1 * | 8/2015 | Forsell | A61F 2/04 | 600/30 |
| 2016/0310711 A1 * | 10/2016 | Luxon | A61B 5/4839 | |
| 2017/0080422 A1 * | 3/2017 | Maaskant | B01D 17/0217 | |
| 2018/0164221 A1 * | 6/2018 | Singh | A61B 5/4238 | |
| 2018/0168490 A1 * | 6/2018 | Jones | A61B 5/002 | |
| 2018/0353020 A1 * | 12/2018 | Stapleton | A61F 5/455 | |
| 2018/0355894 A1 * | 12/2018 | Brevet | B25J 9/144 | |
| 2019/0247050 A1 * | 8/2019 | Goldsmith | A61B 17/00491 | |

* cited by examiner

US 10,687,676 B2

MICROGRAVITY URINE COLLECTION AND STORAGE

FIELD

The present disclosure relates to waste processing systems, and more specifically, to microgravity urine collection and storage.

BACKGROUND

A conventional Universal Waste Management System (UWMS), such as the system used for deep space exploration, has no-fault tolerance. In other words, if a component of the UWMS were to fail, the crew would be unable to operate the UWMS. In other space craft, such as those used for Low Earth Orbit (LEO) travel, the crew wears diapers for urine collection, which are uncomfortable and require a diaper inventory to be loaded in the space craft, which adds weight.

SUMMARY

In various embodiments, the present disclosure provides a microgravity urine collection apparatus that includes a bellows defining an internal chamber having a selectively adjustable volume, the bellows comprising an inlet and an outlet. The microgravity urine collection apparatus may further include a first valve coupled to the bellows and configured to selectively control fluid flow through the inlet. The microgravity urine collection apparatus may also include a second valve coupled to the bellows and configured to allow fluid flow out of the bellows via the outlet and prevent fluid flow into the bellows via the outlet.

In various embodiments, expansion of the bellows increases the selectively adjustable volume of the internal chamber for entraining fluid into the internal chamber via the inlet. In various embodiments, contraction of the bellows decreases the selectively adjustable volume of the internal chamber for expelling fluid out of the internal chamber via the outlet. The first valve may be a gate valve and the second valve may be a check valve. The gate valve may be normally in a closed position to prevent fluid flow into the internal chamber of the bellows and is configured to be manually actuated to an open position to allow fluid flow into the internal chamber of the bellows. The gate valve may include a spring-loaded gate element having an obstruction portion an aperture portion, wherein in the closed position the obstruction portion of the spring-loaded gate element is aligned with the inlet of the bellows and in the open position the aperture portion is at least partially aligned with the inlet of the bellows.

In various embodiments, the microgravity urine collection apparatus further includes a funnel attachment coupled to the first valve, wherein the funnel attachment is configured to facilitate entrainment of urine. In various embodiments, the funnel attachment comprises an elongated and curved opening for engaging a vulva of a female user. In various embodiments, a nominal volume of the internal, expanded chamber is about 1 liter.

Also disclosed herein, according to various embodiments, is a microgravity urine storage apparatus that includes a housing, a bellows, an absorbent medium and a retention feature. The housing may define an internal cavity having a fixed volume and the housing may include a housing inlet and a housing outlet. The bellows may define an internal chamber having an adjustable volume and the bellows comprising a bellows inlet and a bellows outlet. The absorbent medium may be disposed within the internal chamber of the bellows and the absorbent medium configured to absorb urine. The retention feature may be mounted to the housing and may be selectively deployable in a retention mode and a released mode. In the retention mode the retention feature engages and secures the bellows in a contracted state and in the released mode the retention feature is disengaged from the bellows to allow expansion of the bellows in response to urine absorption by the absorbent medium, according to various embodiments.

In various embodiments, the retention feature is configured to be in the retention mode during and throughout a spacecraft launch event and is configured to be manually switched to the released mode in orbit. In various embodiments, the absorbent medium includes a super absorbent polymer material. The microgravity urine storage apparatus may further include a hydrophobic membrane disposed within the housing between the bellows outlet and the housing outlet. The microgravity urine storage apparatus may further include a vapor filter disposed within the housing between the hydrophobic membrane and the housing outlet. The vapor filter may be a charcoal filter. The charcoal filter may absorb odors, and trap small amounts of urine that may pass through the hydrophobic membrane.

Also disclosed herein, according to various embodiments, is a microgravity urine collection system that includes the microgravity urine collection apparatus coupled to the microgravity urine storage apparatus.

The forgoing features and elements may be combined in various combinations without exclusivity, unless expressly indicated herein otherwise. These features and elements as well as the operation of the disclosed embodiments will become more apparent in light of the following description and accompanying drawings.

Figure 1:
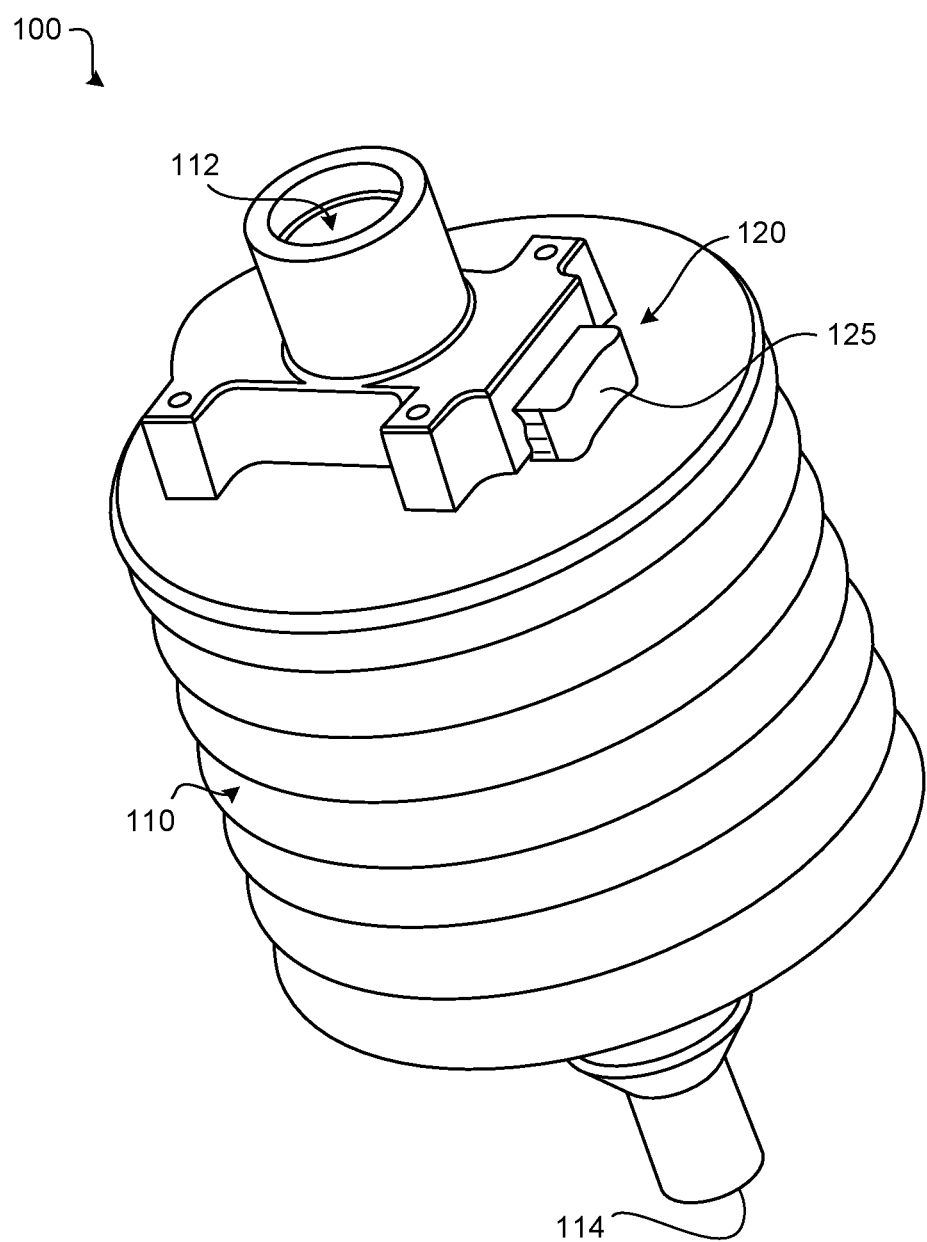
FIG. 1 illustrates a perspective view of a microgravity urine collection apparatus, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

Figure 2:
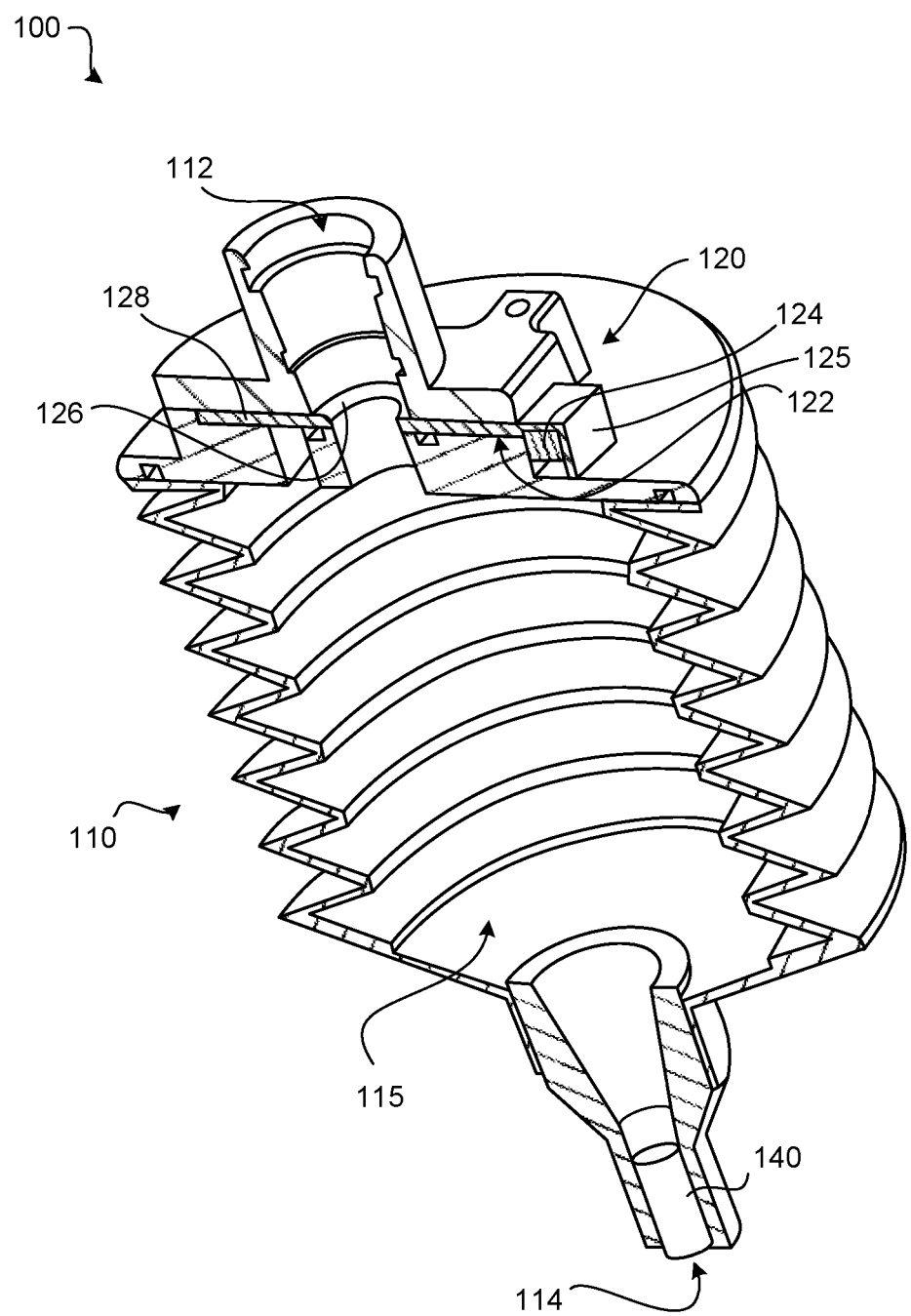
FIGS. 2 and 3 illustrate cross-sectional views of the microgravity urine collection apparatus of FIG. 1, in accordance with various embodiments.
Figure 3:
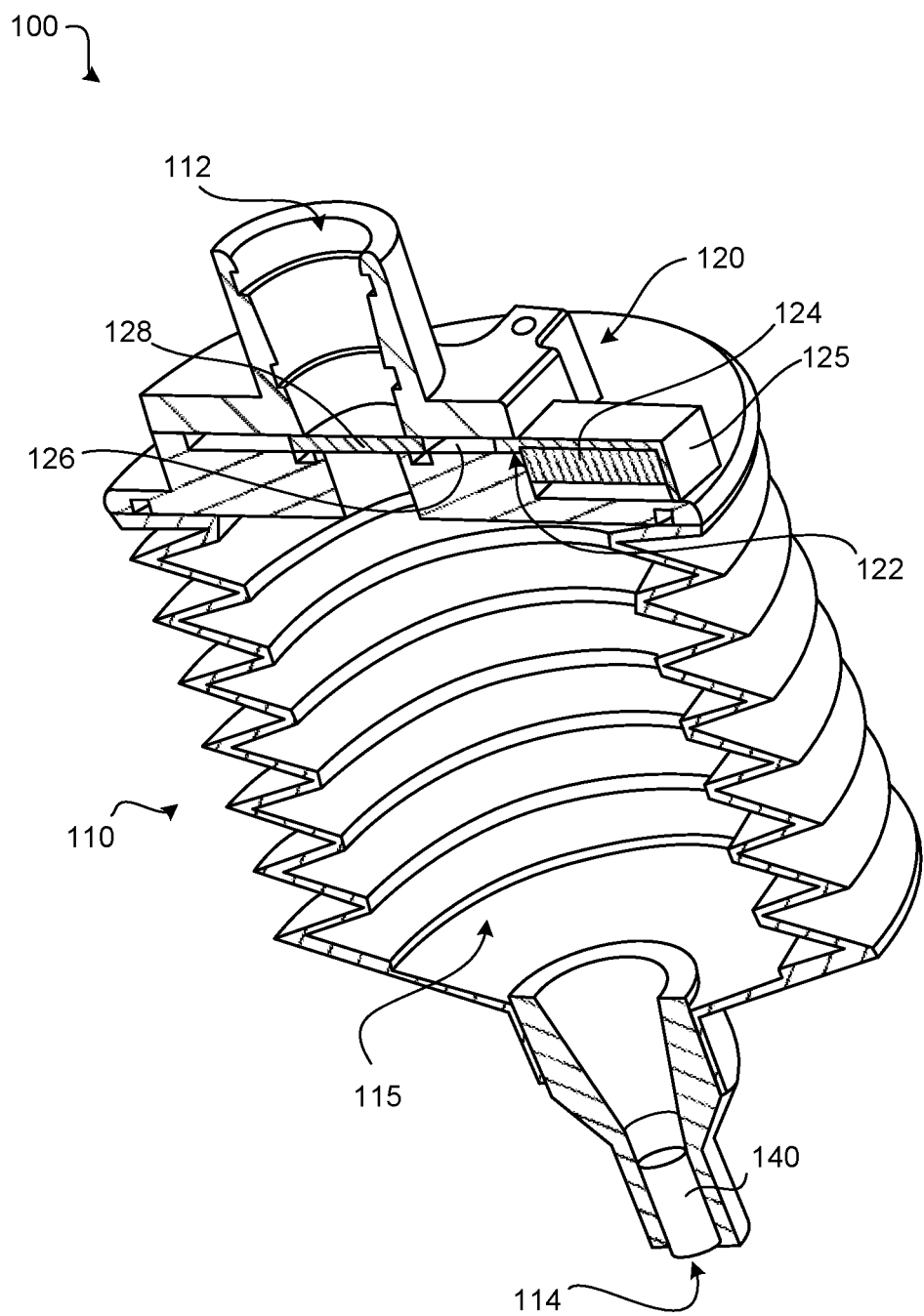

In various embodiments, and with reference to FIGS. 1, 2, and 3, a microgravity urine collection apparatus 100 is provided. The microgravity urine collection apparatus 100, as described in greater detail below, is generally a manual urine collection device. The microgravity urine collection apparatus 100 may be utilized in conjunction with, for example, the microgravity urine storage apparatus 200 described below with reference to FIGS. 5, 6, and 7. These apparatuses 100, 200 may be implemented for use within various spacecraft, such as the International Space Station (ISS), low earth orbit (LEO) aircraft, crew exploration vehicles (CEV), and/or a space hotel. Stated another way, the microgravity urine collection apparatuses and systems disclosed herein may supplement, replace, and/or be utilized in conjunction with existing aerospace waste collector systems.

In various embodiments, and with reference to FIGS. 1, 2, and 3, the microgravity urine collection apparatus 100 may include a bellows 110, a first valve 120, and a second valve 140. The bellows 110 has an inlet 112 and an outlet 114 and generally defines an internal chamber 115, according to various embodiments. The internal chamber may have a selectively adjustable volume. Said differently, the bellows 110 may be manually expanded and contracted (e.g., by a crew member of a space craft) to change the volume of the internal chamber 115. Such volume changes affect the pressure within the internal chamber 115, which causes fluid, such as urine, to be entrained and expelled, respectively. In various embodiments, a nominal volume of the internal chamber 115 is about 1 liter. Additional details regarding entrainment and expulsion of urine are included below.

The first valve 120 may be coupled to the bellows 110 and may be configured to selectively control fluid flow through inlet 112. The second valve 140 may be coupled to the bellows 110 and may be configured to allow fluid flow out of the bellows 110 via the outlet 114. The second valve 140 may prevent fluid flow into the bellows 110 via the outlet 114. The valves 120, 140 may form a portion or an end wall of the bellows 110, and/or the valves 120, 140 may be disposed, at least partially, in the inlet 112 and outlet 114 portions of the bellows 110.

In various embodiments, the first valve 120 may be a gate valve. The first valve 120 may be normally in a closed position (i.e., may be biased so as to be closed if a user is not actively actuating the valve) to prevent fluid flow into the internal chamber 115 of the bellows 110. The first valve 120 may be configured to be manually actuated to an open position to allow fluid flow into the internal chamber 115 of the bellows 110. For example, the first valve 120 may include a biasing element 124, such as a spring, that biases a spring-loaded gate element 122 to be in a default, at-rest position (e.g., closed position). The spring-loaded gate element 122 may be configured to translate between the closed position and an open position. The spring-loaded gate element 122 may include an obstruction portion 128 and an aperture portion 126. In the closed position illustrated in FIG. 3, the obstruction portion 128 may block the inlet 112 to prevent fluid flow into or out from the bellows 110 via the inlet 112. Alternatively, in the open position illustrated in FIG. 2, the aperture portion 126 may be at least partially aligned with the inlet 112 to allow fluid flow into (or inadvertently out from) the bellows 110 via the inlet 112.

The second valve 140 may be a check valve that only allows fluid flow in a desired direction (i.e., allows flow out of the internal chamber 115 via the outlet 114) and prevents fluid flow in an opposite direction (i.e., prevents flow into the internal chamber 115 via the outlet 114).

In operation of the microgravity urine collection apparatus 100, a user may preemptively expand the bellows 110 to reduce the pressure within the internal chamber 115 in preparation for urinating. As urination begins (or just before), the user may position the inlet 112 of the bellows 110 in proximity to his/her crotch and the user may actuate the first valve 120 (e.g., by pushing or pulling on a user engagement tab 125) to move the first valve 120 to the open position (FIG. 2), thereby initiating entrainment of urine and air near the inlet 112. In a microgravity environment, the urine will be drawn and entrained into the internal chamber 115 of the bellows 110 via the inlet 112. The user may, instead of (or in conjunction with) preemptively expanding the bellows 110, continuously and judiciously expand the bellows 110 during urination, thereby creating a continuous draw of urine and air into the bellows 110. The suction created by expanding the bellows 110 may also be used to remove any residual urine from the crew members body to enhance cleanliness. Upon termination of urination, or if additional suction is required, the user may again actuate the first valve 120 to return the control surface of the first valve 120 to the closed position. In various embodiments, in response to the user releasing the user engagement tab 125, the spring or other biasing element may force the control surface, such as the gate element, to the closed position. By so doing, the user prevents fluid flow into or out of the inlet 112, and the user may contract/compress the bellows 110. In response to contraction of the bellows 110, the second valve 140, which may be a check valve or other directional flow control device, permits the entrained fluid (i.e., air and urine) to be expelled through the second valve 140 and out through the outlet 114 of the bellows 110. Compressing the bellows 110 creates a pumping pressure that is used to force the air/urine mixture towards the second bellows.

Figure 4:
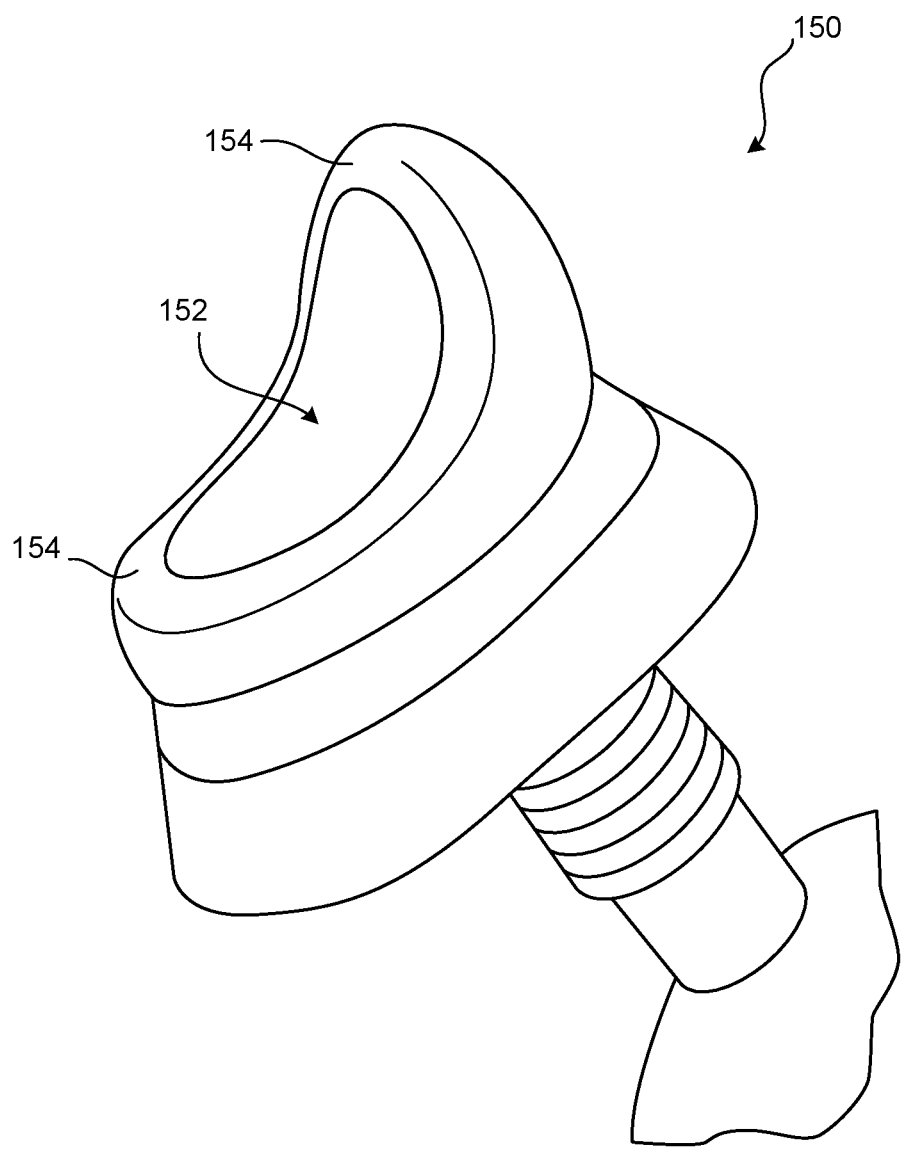
FIG. 4 illustrates a perspective view of a funnel attachment for a microgravity urine collection apparatus, in accordance with various embodiments.

In various embodiments, and with reference to FIG. 4, the microgravity urine collection apparatus 100 may further include a funnel attachment 150 that may be coupled to the first valve 120 and/or the inlet 112 of the bellows 110. The funnel attachment 150 may be useful for facilitating the entrainment of urine. In various embodiments, the funnel attachment 150 includes an elongated and curved opening 152 defined by a rim 154 that engages a crotch/vulva of a female user.

Figure 5:
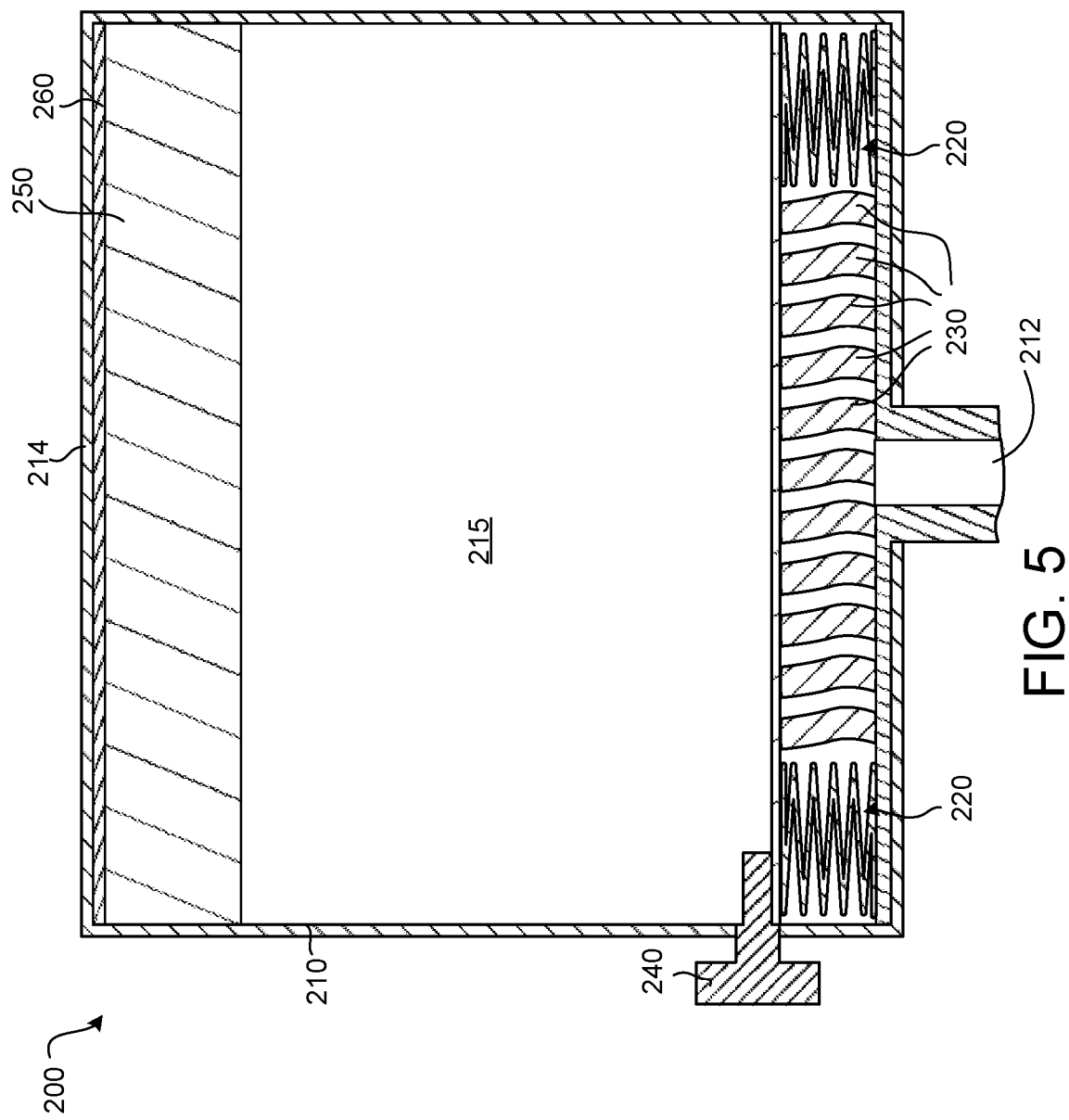
FIGS. 5 and 6 illustrate cross-sectional views of a microgravity urine storage apparatus, in accordance with various embodiments.
Figure 6:
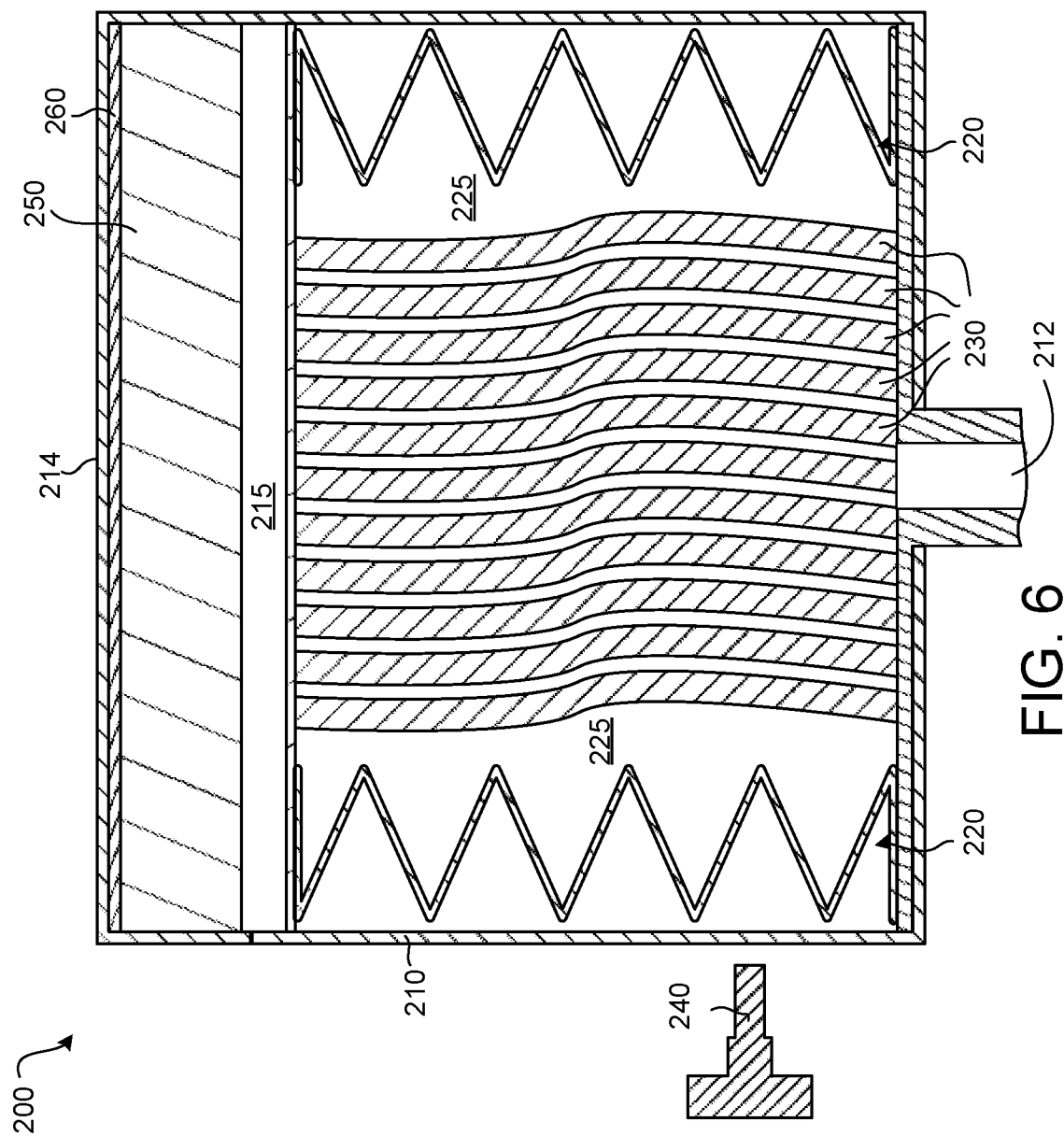

In various embodiments, and with reference to FIGS. 5 and 6, a microgravity urine storage apparatus 200 is provided. The microgravity urine storage apparatus 200 may be positioned downstream of the microgravity urine collection apparatus 100 described above. In other words, the microgravity urine storage apparatus 200 is generally configured to receive the manually expelled urine and air from the microgravity urine collection apparatus 100, retain and store the liquid urine, and then reuse/recycle the air, according to various embodiments.

In various embodiments, the microgravity urine storage apparatus 200 includes a housing 210, a bellows 220, an absorbent medium 230, and a retention feature 240. Bellows 110 described above with reference to FIGS. 1, 2, and 3 may be referred to herein as a "first bellows 110," and bellows 220 of FIGS. 5 and 6 may be referred to herein as a "second bellows 220." In other words, in order to avoid confusion between the first bellows 110 of the microgravity urine collection apparatus 100 and the second bellows 220 of the microgravity urine storage apparatus 200, the components of each bellows 110, 220 may be labeled and referred to herein using the adjectives "first" and "second," respectively. Accordingly, the previously described components of the first bellows 110 may be referred to herein as the first bellows inlet 112, the first bellows outlet 114, the first bellows internal chamber 115, etc.

The housing 210 may define an internal cavity 215 having a fixed volume. The housing 210 may also include a housing inlet 212 and a housing outlet 214. In various embodiments, the second bellows 220 defines a second internal chamber 225 that has an adjustable volume. The second bellows 220 may also include a second bellows inlet and a second bellows outlet that are at least partially aligned with the respective inlet 212 and outlet 214 of the housing 210. In various embodiments, volume of the second internal chamber 225 is not configured to be adjusted directly. Said differently, whereas the volume of first internal chamber 115 of the first bellows 110 is manually and selectively adjustable, the volume of the second internal chamber 225 of the second bellows 220 may be indirectly controlled by the expulsion of urine and air from the first bellows 110 to inlet 212 of the housing 210 of the microgravity urine storage apparatus 200 (e.g., via conduit 55, with momentary reference to FIG. 7).

In various embodiments, the absorbent medium 230 is disposed within the internal chamber 225 of the second bellows 220 and is configured to absorb urine and/or other liquids. In various embodiments, the absorbent medium 230 is a Superabsorbent Polymer (SAP) that can absorb and retain large amounts of liquid relative to its mass and volume.

In various embodiments, on or more retention features 240 are mounted to the housing 210 and are selectively deployable in a retention mode (FIG. 5) or a released mode (FIG. 6). In the retention mode, the retention feature 240 may engage and secure the second bellows 220 in a contracted state. In the released mode, the retention feature 240 is disengaged form the second bellows 220, thereby allowing the second bellows 220 to expand in response to urine flowing into the housing 210 and into the second bellows 220 from the microgravity urine collection apparatus 100. For example, in the retention mode the retention feature 240 may protrude into the housing 210 and engage a top edge of the bellows to keep the bellows 220 in the contracted state. In other words, in the released mode (FIG. 6), as urine enters the second bellows 220 the absorbent medium 230 may expand and the second bellows 220 may correspondingly expand.

In various embodiments, the retention features 240 is configured to be in the retention mode during and throughout a spacecraft launch event in order to prevent excess vibration of the bellows 220 and/or absorbent medium 230 within the housing 210. Once the space craft is in orbit, a user may manually switch the retention feature 240 to the released mode, thereby allowing the aforementioned expansion. The retention feature 240, or a secondary retention feature, may be utilized to again retain the bellows 220 and/or the absorbent medium 230 a secure/retained configuration during reentry, thus preventing excess vibration during a return trip.

In various embodiments, the microgravity urine storage apparatus 200 further includes a hydrophobic membrane 250 disposed within the housing 210 between the bellows 220 and the housing outlet 214. The hydrophobic membrane 250 may further facilitate the liquid-gas separation and may prevent liquid from passing beyond the hydrophobic membrane 250. In various embodiments, the microgravity urine storage apparatus 200 may further include a vapor filter 260, such as a charcoal filter, disposed within the housing 210. The vapor filter 260 may be disposed between the hydrophobic membrane 250 and the housing outlet 214.

Figure 7:
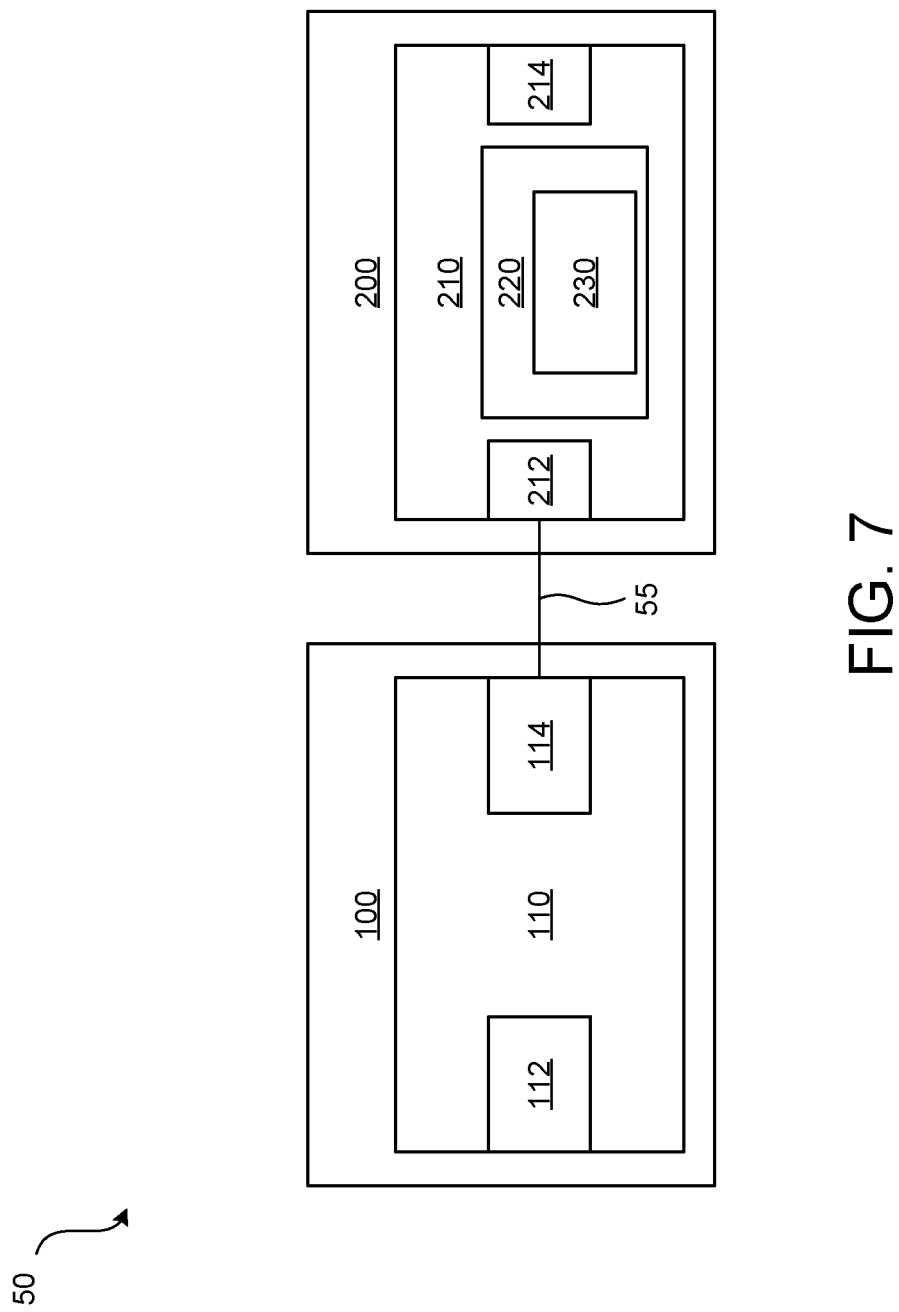
FIG. 7 is a schematic block diagram of a microgravity urine collection system, in accordance with various embodiments.

In various embodiments, and with reference to FIG. 7, the two apparatuses 100, 200 may be coupled together via conduit 55 to form a microgravity urine collection system 50. As mentioned above, expansion of the first bellows 110 increases the selectively adjustable volume of the first internal chamber in order to entrain urine into the first internal chamber 115 via the first bellows inlet 112. Subsequent contraction of the first bellows 110 decreases the selectively adjustable volume of the first internal chamber 115 and thus expels the urine out of the first internal chamber 115 via the first bellows outlet 114 and into the second internal chamber of the second bellows 220 via the housing inlet 212 and the second bellows inlet.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A microgravity urine collection apparatus comprising:
   a bellows defining an internal chamber having a selectively adjustable volume, the bellows comprising an inlet and an outlet;
   a first valve coupled to the bellows and configured to selectively control fluid flow through the inlet; and
   a second valve coupled to the bellows and configured to allow fluid flow out of the bellows via the outlet and prevent fluid flow into the bellows via the outlet;
   wherein the first valve is configured to be manually actuated to an open position to allow fluid flow into the internal chamber of the bellows;
   wherein the first valve comprises a spring-loaded gate element having an obstruction portion and an aperture portion;
   wherein, in a closed position, the obstruction portion of the spring-loaded gate element blocks the inlet of the bellows;
   wherein, in the open position, the aperture portion is at least partially aligned with the inlet of the bellows; and
   wherein the second valve is a check valve.

2. The microgravity urine collection apparatus of claim 1, wherein:
   expansion of the bellows is configured to increase the selectively adjustable volume of the internal chamber for entraining fluid into the internal chamber via the inlet; and
   contraction of the bellows is configured to decrease the selectively adjustable volume of the internal chamber for expelling fluid out of the internal chamber via the outlet.

3. The microgravity urine collection apparatus of claim 1, wherein the first valve is a gate valve.

4. The microgravity urine collection apparatus of claim 1, wherein the first valve is configured to prevent fluid flow into the internal chamber of the bellows.

5. The microgravity urine collection apparatus of claim 1, further comprising a funnel attachment coupled to the first valve, wherein the funnel attachment is configured to facilitate entrainment of urine.

6. The microgravity urine collection apparatus of claim 5, wherein the funnel attachment comprises an elongated and curved opening for engaging a vulva of a female user.

7. The microgravity urine collection apparatus of claim 1, wherein a nominal volume of the internal chamber is about 1 liter.

8. A microgravity urine storage apparatus comprising:
   a housing defining an internal cavity having a fixed volume, the housing comprising a housing inlet and a housing outlet;
   a bellows located within the housing, the bellows defining an internal chamber having an adjustable volume, the bellows comprising a bellows inlet and a bellows outlet;
   an absorbent medium disposed within the internal chamber of the bellows, the absorbent medium configured to absorb urine;
   a retention feature mounted to the housing, wherein the retention feature is selectively deployable in a retention mode and a released mode, wherein in the retention mode the retention feature secures the bellows in a contracted state, and wherein in the released mode the retention feature is disengaged from the bellows; and
   a hydrophobic membrane disposed within the housing but outside of the internal chamber of the bellows, wherein the hydrophobic membrane is disposed between the bellows outlet and the housing outlet.

9. The microgravity urine storage apparatus of claim 8, wherein the retention feature is configured to be in the retention mode during and throughout a spacecraft launch event and is configured to be manually switched to the released mode in orbit.

10. The microgravity urine storage apparatus of claim 8, wherein the absorbent medium comprises a super absorbent polymer material.

11. The microgravity urine storage apparatus of claim 8, further comprising a vapor filter disposed within the housing but outside of the internal chamber of the bellows, wherein the vapor filter is disposed between the hydrophobic membrane and the housing outlet.

12. The microgravity urine storage apparatus of claim 11, wherein the vapor filter is a charcoal filter configured to absorb odor.

13. A microgravity urine collection system comprising:
   a first bellows defining a first internal chamber having a selectively adjustable volume, the first bellows comprising a first bellows inlet and a first bellows outlet;
   a first valve coupled to the first bellows and configured to selectively control fluid flow through the first bellows inlet;
   a second valve coupled to the first bellows and configured to allow fluid flow out of the first bellows via the first bellows outlet and prevent fluid flow into the first bellows via the first bellows outlet;
   a housing defining an internal cavity having a fixed volume, the housing comprising a housing inlet and a housing outlet;

a conduit fluidly coupling the first bellows outlet of the first bellows to the housing inlet;

a second bellows located within the housing, the second bellows defining a second internal chamber having an adjustable volume, the second bellows comprising a second bellows inlet and a second bellows outlet, wherein the adjustable volume of the second internal chamber of the second bellows is configured to be indirectly controlled by expulsion of urine and air from the first bellows to the second bellows;

an absorbent medium disposed within the second internal chamber of the second bellows; and a retention feature mounted to the housing that is selectively deployable in a retention mode and a released mode, wherein in the retention mode the retention feature secures the second bellows in a contracted state, and wherein in the released mode the retention feature is disengaged from the second bellows to allow the second bellows to expand in response to the expulsion of urine and air from the first bellows to the second bellows.

14. The microgravity urine collection system of claim 13, wherein:

expansion of the first bellows increases the selectively adjustable volume of the first internal chamber for entraining urine into the first internal chamber via the first bellows inlet; and contraction of the first bellows decreases the selectively adjustable volume of the first internal chamber for expelling the urine out of the first internal chamber via the first bellows outlet and into the second internal chamber of the second bellows via the housing inlet and the second bellows inlet, thereby causing expansion of the second bellows.

15. The microgravity urine collection system of claim 13, further comprising a funnel attachment coupled to the first valve, wherein the funnel attachment is configured to facilitate entrainment of urine.

16. The microgravity urine collection system of claim 13, wherein the retention feature is configured to be in the retention mode during and throughout a spacecraft launch event and is configured to be manually switched to the released mode in orbit.

17. The microgravity urine collection system of claim 13, further comprising a hydrophobic membrane disposed within the housing between the second bellows outlet and the housing outlet.

* * * * *